United States Patent [19]

Tenney et al.

[11] 4,309,388

[45] Jan. 5, 1982

[54] OZONE STERILIZING APPARATUS

[76] Inventors: Robert I. Tenney, 32 Coldstream Cir., Deerfield, Ill. 60015; William R. Eckstrom, 14709 Kenwood, Dolton, Ill. 60419

[21] Appl. No.: 118,655

[22] Filed: Feb. 4, 1980

[51] Int. Cl.³ .......................... A61L 2/10; A61L 2/20
[52] U.S. Cl. ..................... 422/304; 422/24; 422/29; 422/30; 422/117; 422/302; 250/453; 250/455
[58] Field of Search ............... 422/24, 29, 117, 302, 422/304, 30; 250/453, 455, 533, 532

[56] References Cited

U.S. PATENT DOCUMENTS

| | | | |
|---|---|---|---|
| 1,984,457 | 12/1934 | Buttolph | 422/24 X |
| 2,056,614 | 10/1936 | Moehler | 250/453 |
| 2,085,573 | 6/1937 | Buttolph | 422/24 X |
| 2,212,330 | 8/1940 | Thomas | 250/453 |
| 2,537,530 | 1/1951 | Hofman | 422/24 X |

*Primary Examiner*—Barry Richman

[57] ABSTRACT

Sterilizing apparatus preferably comprises an enclosure surrounding the top, bottom and sides of a central sterilizing enclosure space and adjacent inlet and outlet enclosure spaces opening horizontally to the exterior of the enclosure at the opposite ends thereof. A continuously moving conveyor carries open-topped containers to be sterilized horizontally through the inlet, sterilizing and outlet enclosure spaces of the enclosure. The sterilizing enclosure space is divided by partition walls into an upper compartment which opens at the bottom thereof into a lower compartment immediately above the path of travel of the open tops of the containers passing through the lower compartment of the sterilizing enclosure space. Ozone-generating ultraviolet lamps are mounted in the upper compartment, and a blower circulates air between the lower and upper compartments and through the opening of the upper compartment into the lower compartment so that ozone generated in the upper compartment is directed into the openings at the tops of the containers moving in the lower compartment. Ozone decomposition accelerating ultraviolet lamps are positioned in the inlet and outlet enclosure spaces to accelerate decomposition of the ozone in the air escaping to the surrounding atmosphere through the inlet and outlet enclosure spaces.

12 Claims, 4 Drawing Figures

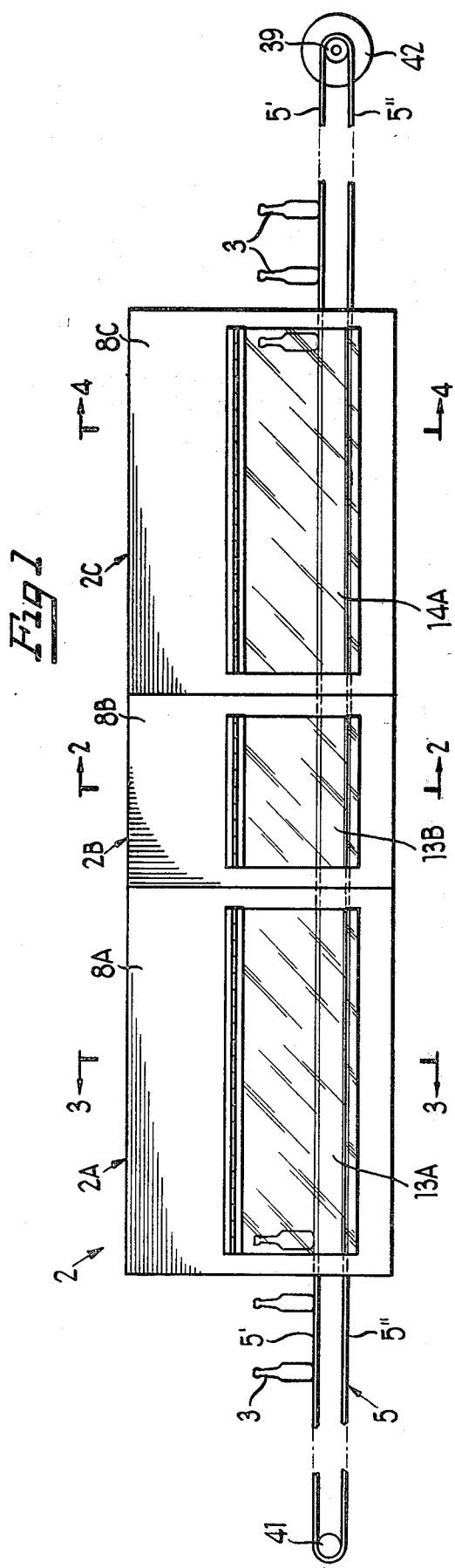
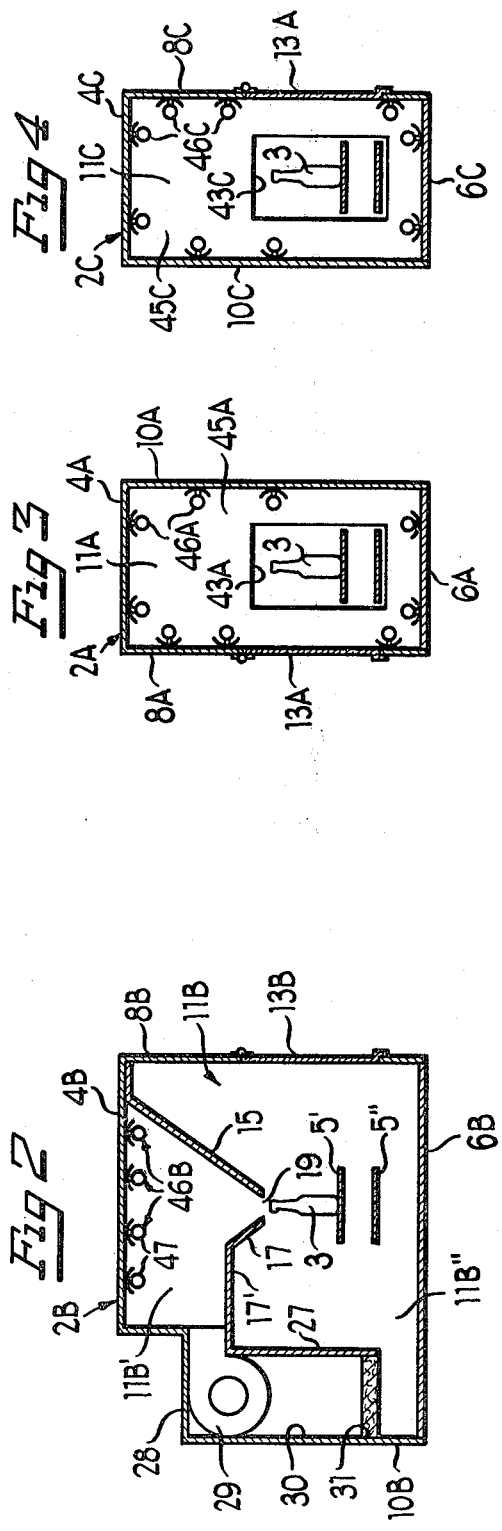

OZONE STERILIZING APPARATUS

BACKGROUND OF INVENTION

This invention relates to apparatus for sterilizing bottles, cans and other containers using activated oxygen (ozone) in such a manner that the ozone produced is destroyed or reduced to a non-irritating and harmless concentration in the work area surrounding the apparatus.

Beverages and similar fluids are commonly packaged in bottles, cans, or cartons for distribution to consumers. Such containers are commonly delivered empty along a conveyor line to a filling device and then proceed to equipment which affixes a cap, crown, crimp or other closing device to the container. While it is highly desirable that these containers be sterile at the time they reach the filling device, such sterility is commonly lacking. In the case of re-useable bottles which are washed between uses, most often they are washed in hot caustic solutions which cleanse and sterilize the bottles. However, the caustic solution must be rinsed from the bottles and the water used for this purpose may be of potable quality but not necessarily sterile. Accordingly, the rinse water often contains living microorganisms which can spoil the liquid in the container. Beer, milk, vegetable and fruit juices all contain nutrients capable of supporting microbial growth under such non-sterile conditions.

New bottles are also seldom subjected to effective sterilizing conditions immediately prior to filling. While glass and synthetic plastic bottles are formed from hot melts which would insure sterility at the instant they leave the mold, from that time on they are subjected to annealing and/or cooling air currents and are conveyed through possibly dusty areas to be packed into containers and shipped under conditions substantially less than sterile.

Metal cans are formed in equipment which must be lubricated with coolants notorious for their high bacteria counts. This coolant is rinsed away in a stream of water, and, while the rinse water is often sterile, it has no residual sterilizing effect on any bacteria present in the package. Paper cartons and other containers are similarly lacking in the inherent sterility one would like to count upon in the quality packaging of most beverages.

Ultraviolet radiation is known to have germicidal properties and has, accordingly, been used to sterilize various articles including bottles. (U.S. Pat. Nos. 2,194,463 and 2,384,770 show the sterilization of bottles through such a means.) Ultraviolet radiation sources which generate ultraviolet radiation wavelengths below about 330 nanometers have germicidal properties which will destroy bacteria on direct exposure to such radiation. However, the germicidal properties of such ultraviolet radiation wavelengths quickly dissipate a short distance from the ultraviolet radiation source, and thus it is necessary to bring ultraviolet lamps generating these wavelengths into immediate continuous relationship to the articles which are sterilized thereby. Since the glass out of which most bottles are made filters out most of the sterilizing ultraviolet radiation generated by the lamps, it is necessary to insert such lamps directly into the bottles involved. Where the shape of the bottles precludes bringing the ultraviolet lamps contiguous to work surfaces of the bottles to be sterilized, the sterilizing results are unsatisfactory. Also, the requirement that the ultraviolet lamps be moved into and out of the bottles makes this bottle sterilizing operation slow, cumbersome and expensive.

It is common to heat bottles to a sterilizing temperature while being filled or after they are filled and capped. The latter method is necessary in the filling of beer bottles where the filling operation cannot take place while the bottles are raised to a pasturizing temperature because of the undesired release of carbon dioxide which would take place under filling conditions. The disadvantages of these bottle heating sterilizing methods is that the sterilizing process involves excessive energy use and costly equipment.

Ozone, a gaseous alatrope of oxygen, is known as a strong oxidant and an effective sterilant. It has been commonly used to sterilize water, but is only rarely used to sterilize other materials (e.g. Russian Pat. No. 279,895 discloses the use of ozone to sterilize medical instruments). Ozone has the advantage that once it is introduced into any container, it completely fills it, so as to reach all interior surfaces, where it will destroy any contaminating microorganisms that might be present.

It is known that ozone can be generated most efficiently by ultraviolet radiation having wavelengths below about 200 nm. Thus, ultraviolet radiation sources producing wavelengths of about 180 nm produce ozone efficiently. Ultraviolet lamps which are made with a quartz envelope will pass ultraviolet energy wavelengths centered around 185 nm to a maximum degree and, therefore, are very useful in producing ozone.

While initial efforts by us to use ultraviolet radiation at these wavelengths directed over bottles in a partially enclosed space produces ozone which sterilized the inner surfaces of the bottles, these efforts were unsatisfactory because appreciable ozone escaped into the surrounding atmosphere in irritating and possibly harmful quantities.

SUMMARY OF THE INVENTION

In accordance with one aspect of our invention, a sterilizing apparatus enclosure is uniquely designed so that the ozone is applied to the interior of the containers to be sterilized in a manner which most efficiently uses the ozone fed to or produced in the sterilizing apparatus enclosure. Another aspect of the invention is that the ozone sterilizing apparatus is designed so that the containers involved can be continuously fed through the sterilizing apparatus enclosure by a continuously operating conveyor moving through the enclosure open at the opposite ends thereof, and further wherein the sterilizing apparatus is designed so that the air escaping from the sterilizing apparatus through the inlet and/or outlet openings of the enclosure thereof contain little or no ozone which can cause irritation or harm to persons even in the immediate area of the sterilizing apparatus.

In accordance with the preferred form of the former aspect of the invention, the sterilizing apparatus enclosure includes a support for the containers to be sterilized where the containers are aligned with their open ends facing in the same direction in a sterilizing enclosure space. The sterilizing enclosure space is divided by partition walls into adjacent compartments with a passageway therebetween opening onto the path of travel of the open ends of the containers passing through one of the compartments. Blower means circulates air between these compartments and through said passageway so that the air stream is directed into the open ends of the aligned containers. This passageway may be defined by a longitudinal opening in partition walls separating these adjacent compartments. Ozone is preferably generated in this circulating air stream by ultraviolet lamps producing useful radiation at wavelengths at or below about 200 nm and positioned in the compartment where the blower forces the air through said passageway, so that the ozone is produced close to the points in the adjacent compartment where the containers are to be sterilized and the degree of ozone decomposition prior to the points of sterilization is minimized. Said partition walls act to direct and confine the ozone containing air stream to the path of travel of the open ends of the containers so that the ozone is used most efficiently.

In accordance with another aspect of the invention, which does not necessarily require the arrangement of the sterilizing enclosure space walls as just described, although such an arrangement is definitely preferred, ozone decomposition accelerating means are located between the sterilizing enclosure space and any openings of the enclosure involved through which air from the sterilizing enclosure space escapes to the exterior of the enclosure, so that by the time this air reaches such openings there is little or no ozone left which can cause an irritating or harmful condition to persons in the vicinity of the enclosure.

The enclosure most preferably has top, bottom and side walls defining a centrally disposed sterilizing enclosure space and inlet and outlet enclosure spaces on opposite ends of the sterilizing enclosure space and opening horizontally to the exterior of the enclosure at the opposite ends thereof. A continuously moving conveyor preferably carries open-top containers supported on the top of the conveyor which moves the containers horizontally through the inlet, sterilizing and outlet enclosure spaces described. In such case, the ozone decomposing accelerating means referred to are located within the inlet and outlet enclosure spaces and most advantageously are ultraviolet lamps which radiate ultraviolet wavelengths substantially above 200 nm where ozone decomposition is greatly accelerated. Ultraviolet lamps having a mercury vapor therein and a boron-containing pyrex glass envelope efficiently radiate ultraviolet wavelengths of 253.7 nm. (Mercury vapor ultraviolet generating sources produce strong mercury line ultraviolet wavelengths at both 185 and 253.7 nm.)

While ozone used to sterilize drinking water has been heretofore decomposed by directing the ozone leaving the water through a conduit heated to a temperature in excess of 180° F., to our knowledge no ozone decomposition acceleration techniques have been heretofore utilized in any way in the sterilizing of bottles or other containers, let alone in the manner of the present invention previously described. In this connection also, while the broader aspects of the invention encompass the use of heat to accelerate decomposition of the ozone in the air moving toward inlet and/or outlet of the sterilizing enclosure, the use of ultraviolet lamps for this purpose and in the manner specifically to be described constitutes an important specific aspect of the present invention, since the use of ultraviolet lamps for this purpose and in the manner described is a less expensive, more efficient and by far less complex means for accomplishing the acceleration of ozone decomposition.

The above and other features and advantages of the invention will become more apparent upon making reference to the specification to follow, the claims and the drawings.

DESCRIPTION OF DRAWINGS

FIG. 1 is an elevational view of a bottle sterilizing unit constructed in accordance with the present invention;

FIG. 2 is a sectional view through the central, ozone generating and bottle sterilizing portions of the sterilizing unit shown in FIG. 1, taken along section line 2—2 therein;

FIG. 3 is a sectional view through an inlet ozone decomposition accelerating portion of the bottle sterilizing unit of FIG. 1, taken along section line 3—3 therein; and FIG. 4 is a sectional view through an outlet ozone decomposition accelerating portion of the sterilizing unit shown in FIG. 1.

DESCRIPTION OF EXEMPLARY FORM OF THE INVENTION SHOWN IN DRAWINGS

There is shown in FIG. 1 an elevational view of a bottle sterilizing unit of the invention which includes a rectangular enclosure 2 comprising an inlet ozone decomposition acceleration portion 2A, a central ozone generating and sterilizing portion 2B of an outlet ozone decomposition accelerating portion 2C arranged in adjacent horizontally spaced relation. Bottles 3 are conveyed horizontally through the enclosure 2 by a belt or other suitable conveyor which supports the bottles with their open ends at the top thereof. The inlet and outlet portions 2A–2C define inlet and outlet enclosure spaces 11A–11C respectively, and, as illustrated, are formed by horizontal top and bottom walls 4A–6A and 4C–6C and spaced vertical side walls 8A–10A and 8C–10C. The side walls 8A–8C are preferably provided with hinged doors 13A–13C formed of a transparent material so that the bottles within the enclosure 2 can be seen from the outside thereof and so that bottles that become wedged or broken on the conveyor can be readily removed from the conveyor. The material out of which the doors are made must, of course, prevent the passage of ultraviolet radiation, while allowing visible light to pass therethrough.

The central ozone generating and sterilizing portion 2B of the enclosure 2 is formed by horizontal top and bottom walls 4B–6B which form a horizontal continuation of the adjacent afore-mentioned top and bottom walls 4A–6A, 4C–6C, and vertical outer side walls 8B–10B which are spaced outwardly of the outer side walls 8A–10A and 8C–10C of the enclosure portions 2A and 2C to define a relatively large sterilizing enclosure space 11B. The space 11B is divided by various partition walls into an upper ozone feeding compartment 11B' and a bottom ozone receiving compartment 11B". As illustrated in FIG. 2, these partition walls include a straight longitudinally extending wall 15 inclining downwardly from one side portion of the top wall 4B, and an inclined longitudinally extending wall 17 spaced from the bottom end of the wall 15 to define a longitudinally extending opening 19 at the bottom of the upper ozone feeding compartment 11B' which opens onto the path of travel of the open tops of the bottles 3 conveyed horizontally and longitudinally through the enclosure 2 by the conveyor 5. The downwardly and inwardly inclining wall 17 is shown extending from a horizontally, longitudinally-extending wall 17' which, like the walls 15 and 17, extend the full length of the central portion 2B of the enclosure 2. The wall 17' joins a vertical, longitudinally extending wall 27 forming with a transverse side wall 28 and outer side wall 10B a blower inlet compartment 30 at the top of which is mounted a blower 29. The blower 29 draws air through a filter-containing inlet opening 31 and forces this air into the upper ozone feeding compartment 11B' where the air passes down through the longitudinal opening 19 into the bottom ozone receiving compartment 11B" immediately above the path of travel of the open tops of the bottles 3.

Ozone generating means is provided for producing ozone in the air forced by the blower 29 through the opening 19 and into the open tops of the bottles 3. This ozone generating means is most preferably a series of ultraviolet lamps 46B having elongated envelopes 47 which are shown extending almost for the full length of the central portion 2B of the enclosure 2. Where the ultraviolet lamps contain mercury vapor, the envelopes 47 are preferably made of quartz, so that mercury-line 185.7 nm wavelength ultraviolet radiation will be efficiently transmitted through the envelope walls where it effectively converts ordinary molecular oxygen in the air circulated by the blower 29 into ozone. While such glass transmits some mercury line 254.7 nm wavelength ozone-decomposing ultraviolet energy, its effect is overpowered by the very efficient ozone-generating 185 nm wavelength radiation.

The conveyor 5 is shown as a belt conveyor comprising horizontally extending upper and lower sections 5' and 5" which extend around suitable drums or sprockets 39 and 41, the drum or sprockets 39 being shown driven by a motor 42. The belt conveyor passes through an inlet opening 43A formed in vertical outer end wall 45A closing off the inner end of the enclosure 2. Similarly, the belt conveyor 5 passes horizontally through a corresponding outlet opening 43C formed in a vertical outer end wall 45C at the outlet end of the enclosure 2.

The various aforementioned enclosure spaces 11A, 11B and 11C open onto each other for substantially their full cross-sectional areas, and so some of the ozone-containing air circulating within the upper and lower compartments 11B' and 11B" of the enclosure space 11B can gain access to the exterior of the enclosure 2 through the inlet and outlet openings 43A and 43C unless the feature of the invention now to be described is utilized. While ozone decomposes by itself with time, significant quantities thereof will remain in the air escaping through the inlet and outlet openings 43A and 43C in the absence of the elements of the invention now to be described. To this end, ultraviolet lamps 46A and 46C are supported on the top, bottom and side walls of the inlet and outlet enclosure portions 2A and 2C. These ultraviolet lamps are different than the ozone-generating lamps 35 utilized in the central sterilizing portion 2B of the enclosure 2. Thus, the lamps 46A and 46C can be ultraviolet lamps with glass envelopes which filter out ultraviolet radiation wavelengths which are efficient ozone-generating wavelengths (namely at or under 200 nm), leaving the ozone decomposition accelerating wavelengths, like 254.7 nm. The lamps 46A and 46C are shown with elongated envelopes extending longitudinally for most of the length of the inlet and outlet enclosure portions 2A and 2C.

The various features of the present invention have thus provided a unique container sterilizing apparatus that most efficiently effectively directs ozone into the openings of containers delivered to the sterilizing enclosure space and prevents harmful and irritating amounts of ozone from escaping to the outside of the sterilizing enclosure.

It should be understood that numerous modifications may be made in the most preferred form of the invention disclosed in the drawings without deviating from the broader aspects of the invention.

We claim:

1. A continuous sterilizing apparatus comprising an enclosure surrounding the top, bottom and sides of a central sterilizing enclosure space and adjacent inlet and outlet enclosure spaces opening horizontally to the exterior of the enclosure at the opposite ends thereof; a conveyor for carrying open-topped containers to be sterilized horizontally through said inlet, sterilizing and outlet enclosure spaces of the enclosure; said sterilizing enclosure space being divided by partition wall means into upper and lower compartments, said conveyor passing through said lower compartment; passageway means between said upper and lower compartment for directing ozone-containing air in said upper compartment downward into said lower compartment immediately above the path of travel of the open tops of the containers passing through said lower compartment; ozone-generating means for producing ozone in said sterilizing enclosure space; and blower means for recirculating ozone-containing air between said compartments in a direction which directs the same downward through said passageway means into the lower compartment so that ozone in the upper compartment is directed under the force of said blower means into the openings at the tops of the containers as well as between the same.

2. The sterilizing apparatus of claim 1, wherein said conveyor means continuously moves the containers through said enclosure.

3. The sterilizing apparatus of claim 1 wherein said ozone generating means are ultraviolet radiation generating means producing radiation wavelengths centered substantially below about 200 nm and said ozone decomposition accelerating ultraviolet radiation generating means producing in said inlet and outlet spaces primarily radiation wavelengths substantially greater than 200 nm.

4. The sterilizing apparatus of claim 3 wherein at least some of the ozone decomposition accelerating means are located immediately above as well as adjacent the bottom of the openings of said inlet and outlet enclosure spaces.

5. The sterilizing apparatus of claim 1 wherein said ozone generating means are ultraviolet radiation means which produces in said sterilizing enclosure space ultraviolet radiation only over a band of wavelengths which result in a net substantial generation of ozone from molecular oxygen in the air.

6. The sterilizing apparatus of claim 1 or 5 wherein there is provided in both said inlet and outlet enclosure spaces ozone decomposition accelerating means which eliminates or substantially reduces the amount of ozone passing into the surrounding atmosphere from the opposite ends of said enclosure, and said ozone decomposition accelerating means are ultraviolet radiation generating means which radiates ultraviolet radiation only over a band of wavelengths which have a net result of accelerating ozone decomposition rather than generating substantial amounts of the same.

7. The sterilizing apparatus of claim 1 wherein said ozone generating means are ultraviolet radiation generating means producing radiation wavelengths centered substantially below about 200 nm.

8. The sterilizing apparatus of claim 1, or 7 wherein said ozone generating means is located and generates ozone in said upper compartment.

9. The sterilizing apparatus of claim 1 or 5 wherein there is provided in both said inlet and outlet enclosure spaces ozone decomposition accelerating means which eliminates or substantially reduces the amount of ozone passing into the surrounding atmosphere from the opposite ends of said enclosure.

10. The sterilizing apparatus of claim 9 wherein said ozone decomposition accelerating means is ultraviolet radiation generating means producing in said inlet and outlet spaces, primarily radiation wavelengths substantially greater than 200 nm.

11. The sterilizing apparatus of claim 9 wherein said ozone generating and ozone decomposition accelerating means are ultraviolet radiation generating means which radiate ultraviolet radiation at different wavelengths which respectively most efficiently generate and accelerate decomposition of ozone.

12. The sterilizing apparatus of claim 11 wherein said ozone decomposition accelerating means comprise ultraviolet lamps with elongated envelopes extending longitudinally along at least the top and sides of each of said inlet and outlet enclosure spaces through which ozone and air from the said sterilizing enclosure space passes.

* * * * *